US010219698B2

(12) United States Patent
Grubis (10) Patent No.: US 10,219,698 B2
(45) Date of Patent: Mar. 5, 2019

(54) ACQUISITION SAMPLE CLOCK SYNCHRONIZATION LEVERAGING A GLOBAL CLOCKING MECHANISM IN A DISTRIBUTED PHYSIOLOGICAL SENSING SYSTEM (71) Applicant: General Electric Company, Schenectady, NY (US)

(72) Inventor: Matthew George Grubis, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 576 days.

(21) Appl. No.: 14/065,546

(22) Filed: Oct. 29, 2013

(65) Prior Publication Data

US 2015/0116130 A1 Apr. 30, 2015

(51) Int. Cl.
*H04Q 9/00* (2006.01)
*G08C 17/00* (2006.01)
*A61B 5/00* (2006.01)
*G16H 40/63* (2018.01)
*G06F 19/00* (2018.01)

(52) U.S. Cl.
CPC ............ *A61B 5/0022* (2013.01); *G06F 19/00* (2013.01); *G16H 40/63* (2018.01); *H04Q 9/00* (2013.01); *H04Q 2209/47* (2013.01)

(58) Field of Classification Search
CPC ............ H04B 7/005; G08C 19/22; H04J 11/00
See application file for complete search history.

(56) References Cited

U.S. PATENT DOCUMENTS

| | | | |
|---|---|---|---|
| 6,496,705 B1* | 12/2002 | Ng et al. .................... 455/502 |
| 2004/0173003 A1* | 9/2004 | Ibane ........................ 73/1.42 |
| 2006/0136768 A1* | 6/2006 | Liu et al. .................. 713/400 |
| 2006/0284621 A1* | 12/2006 | Doi .......................... 324/601 |
| 2008/0095038 A1* | 4/2008 | Chang ................ H04B 7/15542 370/208 |
| 2008/0284599 A1* | 11/2008 | Zdeblick .............. A61B 5/0031 340/572.1 |
| 2009/0005675 A1* | 1/2009 | Grunwald ............. A61B 5/026 600/424 |
| 2011/0066051 A1* | 3/2011 | Moon et al. .................. 600/509 |
| 2012/0068855 A1* | 3/2012 | Matsumura et al. .... 340/870.02 |
| 2013/0053674 A1* | 2/2013 | Volker ........................ 600/389 |
| 2014/0187883 A1* | 7/2014 | Lisogurski ................... 600/324 |

* cited by examiner

*Primary Examiner* — Joseph H Feild
*Assistant Examiner* — Pameshanand Mahase
(74) *Attorney, Agent, or Firm* — Andrus Intellectual Property Law, LLP (57) ABSTRACT A method for wirelessly monitoring physiological data of a patient includes emitting a timing signal from a wireless emitter, receiving a timing signal at a receiver in a wireless patient monitor, recording physiological data from the patient over time at the wireless patient monitor, wherein the time is defined according to the timing signal, and transmitting the physiological data over a wireless network of a healthcare facility. Thereafter, physiological data recorded from two or more wireless patient monitors may be aligned in time according to the timing signal to create an aligned physiological representation for the patient.

16 Claims, 5 Drawing Sheets

ACQUISITION SAMPLE CLOCK SYNCHRONIZATION LEVERAGING A GLOBAL CLOCKING MECHANISM IN A DISTRIBUTED PHYSIOLOGICAL SENSING SYSTEM

BACKGROUND

Prior art physiological data collection for a single patient collected from multiple sensors connected to multiple devices, or patient monitors, has been centralized in a single, wired device. For example, prior art patient data acquisition devices, such as from electrocardiographs, pulse oximeters, and electroencephalographs, have been wired to a monitor at the patient's bedside, or have otherwise been connected to and controlled by a common processor. Thus, in prior art system, the data collection for a patient it is sampled and processed using a single processor synchronized to a single digital clock. Since data sampling has been centrally controlled, data synchronization has not been a problem in such prior art data acquisition systems.

However, as wireless technology becomes more reliable, patient monitors are transitioning to leveraging wireless technology and abandoning such centralized processing and control. Wireless patient monitors eliminate the cumbersome wires between the patient and the monitor, allowing easier access to the patient, easier patient transport, and more freedom for the patient to move around without disturbing the monitoring and/or inadvertently triggering a false alarm. As patient mobility is an integral part of many patient care regimens in all varieties of healthcare environments, wireless monitoring can be very beneficial for patient care. As part of the recovery process, patients are encouraged to periodically stand up and make short trips to the window, the bathroom, etc. Lack of patient mobility can result in physiologic complications such as deep vein thrombosis, infection and an overall prolonged recovery process. Continuous monitoring is preferably provided during these patient mobility events, and wireless patient monitoring can enable that. However, as patient monitoring devices begin leveraging wireless infrastructure, such as Wi-Fi networks, it is important to make sure that the quality of patient monitoring is not degraded and that the monitoring precision is maintained or increased.

SUMMARY

The present invention stems from the inventor's recognition that wireless patient monitors, while being more convenient and comfortable for patients and caregivers, may pose a problem when it comes to data synchronization. Each wireless device may be separate, each having its own battery, receiver, and processor, and each positioned close to the data acquisition site and configured to provide digital sampling and transmission of the sampled physiological data over a network to a centralized location. That separation, or modularization, may pose a problem when it comes to data synchronization because each separate processor has a separate sample clock, meaning that every data collection device has its own timing mechanism that dictates when data is sampled and provides a digital time stamp for the data it collects. Even if the clocks on two independent devices are initially synchronized exactly, they are likely to slowly drift apart and to provide differing sample points and/or time stamps for simultaneously occurring data. Differing sample periods and/or time stamps can pose a problem when the data recorded on independent devices is assimilated together because the data will be misaligned, and thus may provide an incomplete or inaccurate picture of a patient's physiology. A sample clock divergence of even a fraction of a second can cause a significant misalignment in data, especially in data with a high sample rate.

Thus, the present inventor recognized that a simple and robust solution is needed to synchronize data acquisition across all channels and data acquisition devices gathering physiological data from a particular patient. In one embodiment, method for wirelessly monitoring physiological data of a patient includes emitting a timing signal from a wireless emitter and receiving the timing signal at a receiver in a wireless patient monitor. The wireless patient monitor records physiological data from the patient over time, and the wireless patient monitor defines time according to the timing signal. The physiological data is then transmitted over a wireless network of a healthcare facility. At the network, two or more physiological data sets may be received from two or more wireless patient monitors. The network, or a server therein, aligns the two or more physiological data sets in time to create an aligned physiological representation, and then provides the aligned physiological representation to a clinician.

In another embodiment, a method of synchronizing physiological data acquired from a patient on two or more wireless patient monitors includes recording physiological data from the patient at each wireless patient monitor and transmitting the physiological data from each wireless patient monitor over a wireless network of a healthcare facility. Then, at a central processor, a timing signal is identified within the physiological data recorded at each wireless patient monitor, wherein the timing signal is a predetermined signal element present within the physiological data recorded at each wireless patient monitor. The physiological data acquired by each wireless patient monitor are then aligned with one another according to the timing signal to create an aligned physiological representation, which is then provided to a clinician.

A system for wirelessly monitoring physiological data of a patient includes a timing signal emitter, at least one wireless patient monitor, and a central processor. The timing signal emitter is configured to emit a timing signal that this is receivable within close range of the patient, and the central processor is configured to receive and process physiological data transmitted by one or more wireless patient monitors over a wireless network. The at least one wireless patient monitor has a timing signal receiver configured to receive the timing signal, a sensor configured to record a physiological signal from the patient, a digitizer configured to digitally sample the physiological signal recorded by the sensor to create physiological data, and a wireless network transmitter configured to transmit the physiological data over a wireless network of a healthcare facility. The wireless patient monitor is further configured to synchronize the digital sampling of the physiological signal by the digitizer to the timing signal. The central processor receives the physiological data from the one or more wireless patient monitors and aligns the physiological data for the patient according to the timing signal to create an aligned physiological representation.

Other principle features and advantage of the invention will become apparent to those skilled in the art upon review of the following drawings, the detailed description, and the appended claims.

BRIEF DESCRIPTION OF THE DRAWINGS

The drawings illustrate the best mode presently contemplated of carrying out the disclosure. In the drawings.

DETAILED DESCRIPTION

In the present description, certain terms have been used for brevity, clarity and understanding. No unnecessary limitations are to be implied therefrom beyond the requirement of the prior art because such terms are used for descriptive purposes only and are intended to be broadly construed. The different systems and methods described herein may be used alone or in combination with other systems and methods. Various equivalents, alternatives, and modifications are possible within the scope of the appended claims. Each limitation in the appended claims is intended to invoke interpretation under 35 USC § 112, paragraph (f), only if the terms "means for" or "step for" are explicitly recited in the respective limitation.

Figure 1:
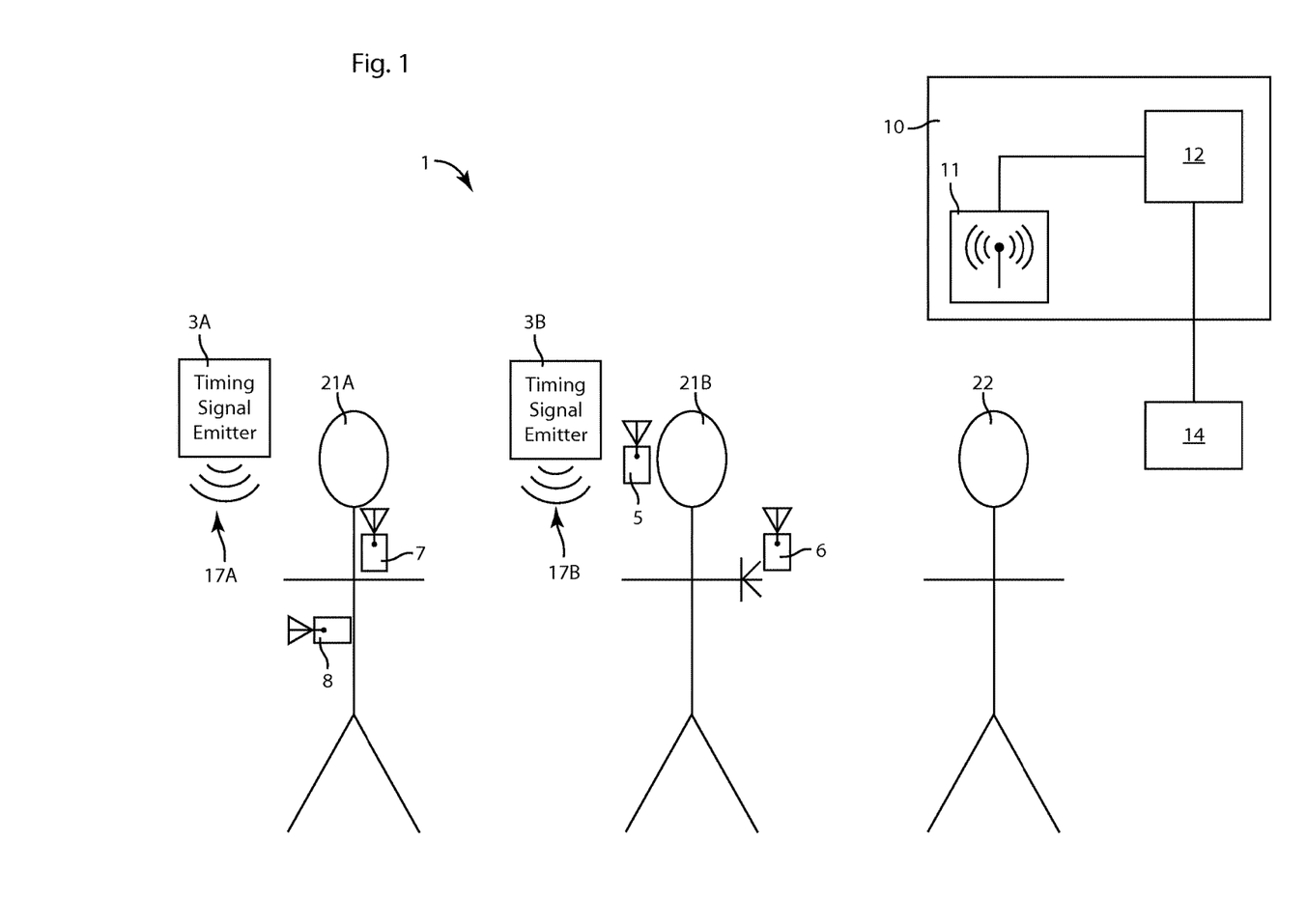
FIG. 1 depicts one embodiment of a system for wireless patient monitoring.

Referring to FIG. 1, a monitoring system 1 includes one or more timing emitters 3 that emit a timing signal 17 that is received by one or more wireless patient monitors 5-8 recording physiological data from one or more patients 21. Each wireless patient monitor 5-8 receives the timing signal 17 and records or synchronizes its data collection thereto. For example, each wireless patient monitor may have a high-speed digitizer that uses an internal sample clock to determine the rate to acquire data. As is explained in more detail below, in such an embodiment the wireless patient monitor synchronizes the internal sample clock to the timing signal 17. Alternatively, and further in accordance with methods and systems described hereinbelow, the timing signal 17 may act as an external clock source to the digitizer, such that the digitizer responds to the timing signal and samples the physiological signal recorded from the patient at the rate dictated by the timing signal. Each wireless patient monitor 5-8 then transmits the physiological data wirelessly to a network 10, such as the network of a healthcare facility. The network has one or more wireless access points 11 to receive the patient physiological data and transmit the data to one or more network servers 12, where the data is processed, stored, and/or accessed by a clinician. Since each patient monitor connected to a patient synchronizes its data collection to the same timing signal, all of the physiological data recorded for each patient can be aligned together in time at the network server 12 to provide a comprehensive picture of the physiological state of the patient at that time.

The wireless patient monitors may be any type of wireless monitor recording and digitizing any type of physiological signals from the patient. In the embodiment shown in FIG. 1, the wireless patient monitors may be an electroencephalograph (EEG) 5, a pulse oximeter 6, an electrocardiograph (ECG) 7, or an invasive blood pressure monitor 8. Since each of the various patient monitors 5-8 connected to the patient synch to the same timing signal, all of the data collected by the separate monitors can be aligned in time to present coordinated information regarding the physiological state of the patient over time. Alternatively or additionally, the independent wireless patient monitors may be independent sensors, or sensor groups, that comprise part of a larger physiological monitor. For example, the wireless patient monitor may be one EEG lead, or a set of EEG leads, that are connected to a patients head and are recording neurological signal information from the patient. Thus, the timing signal 17 may establish the sample rate, and/or synchronize the sample rate and timing, for each of the EEG leads, or sets of leads. Thereby, the data from each of the leads can be aligned to provide a complete EEG.

In one embodiment, the wireless patient monitors 5-8 utilize the timing signal to define, or synch, their respective internal sampling clocks. The wireless patient monitors 5-8 obtain physiological data from the patient over time, wherein the time is defined according to the timing signal. The wireless patient monitors then transmit the physiological data from the patient over the wireless network 10 of the healthcare facility where it can be processed and stored in a central computer 12. The data can then be accessed by a clinician 22, for example by using a display device 14, such as a personal computer, a touch screen monitor, or a handheld display. Alternatively, the data could be presented to the clinician via an alternative mechanism, such as a head-up display or an auditory mechanism.

As depicted in FIG. 1, a wireless patient monitoring system 1 may have more than one timing signal emitter, such as a first timing signal emitter 3A and a second timing signal emitter 3B. The first timing signal emitter 3A emits a first timing signal 17A and provides a local, or patient-specific, timing signal in connection with patient 21A. Likewise, a second timing signal emitter 3B provides a second timing signal 17B for a second patient 21B. In the depicted embodiment, each monitored patient has a separate timing signal emitter that defines the timing signal for that patient's local ecosystem. Thus, all of the wireless patient monitoring devices connected to that particular patient 21A or 21B, e.g., 5 and 6 or 7 and 8, will synchronize their data collection to the respective timing signal 17A or 17B for that patient.

In a preferred embodiment depicted in FIG. 1, the timing signal emitter 3 emits a patient-specific timing signal 17A, 17B that is relatively weak and will only be received by devices connected to a single patient. In such an embodiment, the timing signal must be strong enough to be received by all monitors 5-6 or 7-8 associated with a particular patient, yet weak enough that it will not be received by wireless patient monitors connected to other patients nearby in a healthcare facility environment. Additionally or alternatively, the timing signal may be encoded such that only intended, or associated monitors leverage the timing signal. In other embodiments, the wireless monitoring system may have a single timing emitter that emits a strong enough timing signal such that wireless patient monitors connected to multiple patients can utilize and sync to the same timing signal. In such an embodiment, the wireless monitoring system 1 may have a single timing emitter 3 for a group of patients positioned near each other, such as in a room or a section in a healthcare facility. In still other embodiments, the wireless patient monitoring system 1 may have a single timing emitter 3 for an entire floor or wing, or even a single emitter for an entire healthcare facility.

In one preferred embodiment, the wireless patient monitors are independent devices that are independently powered, such as by battery, and separately collect and wirelessly transmit the patient data to the central computer 12 of the network 10. Since such wireless patient monitors 5-8 connected to any given patient are separate devices, they may each have an internal sampling clock that dictates their respective sampling and time stamping of the patient data. Each wireless monitoring device then separately transmits the patient data it collects over the wireless network 10, and the central computer 12 must be able to receive these separate patient data sets and be able to correlate in time the various data sets for any given patient. As no sampling clock is perfect, and as sampling clocks have a tendency to drift over time and become slightly slow or slightly fast, the wireless monitoring system 1 provides the timing signal by which all wireless monitors for a given patient can synchronize, providing a way for the central computer 12 to align the data for a given patient in time.

The timing signal may be a constant signal emitted by the timing signal emitter 3, or it may be a periodic signal emitted at predefined times or according to a predefined period. Thereby, the timing signal could function as an internal clock for the wireless patient monitor, such that the timing signal provides the trigger for the wireless patient monitor to sample the signal drawn from the patient. In an embodiment where the timing signal is a continuous signal, the wireless patient monitors may continually receive the timing signal and may continuously define the physiological data acquired from the patient according to the emitted timing signal. For example, the wireless patient monitor 5-8 may be responsive to the continuous timing signal such that the continuous timing signal acts as the sample clock, or provides an external sample clock, for the wireless patient monitor 5-8. In other words, the wireless patient monitor 5-8 may sample the patient data at intervals dictated by the frequency and phase of the continuously received timing signal.

Alternatively, the wireless patient monitors 5-8 may periodically tune in to the continuous timing signals emitted by the timing signal emitter 3. In such an embodiment, the wireless patient monitors 5-8 may each tune in to the timing signal according to their own, respective, programming, and each may only tune in as often as necessary or desired for the particular device. For example, a device having a reliable internal clock and operating at a relatively low sample rate may tune in significantly less often than a device with a less reliable clock and a very high sample rate. In this embodiment, a continuous timing signal provides the benefit of not having to synchronize or coordinate the emission schedule of the timing signal emitter 3 with reception schedule of the receivers in the associated wireless patient monitors 5-8. Since the timing signal is continuously provided, the wireless patient monitors 5-8 are able to tune in according to their own schedule dictated by their own programming.

In yet another embodiment, the timing signal emitter 3 emits a periodic timing signal. In this embodiment, the wireless patient monitors 5-8 are programmed to receive the periodic signal. The periodic signal may be a brief signal emitted at certain times, such as every minute or hour. Alternatively, the periodic timing signal may be continuously emitted for a period of time according to a defined schedule, such as for the first ten seconds of every hour or from 12:00 am to 12:02 am every day. Likewise, the timing signal could be alternately emitted and turned off, such as emitted for one hour and then turned off for one hour. In such an embodiment, the wireless patient monitors may be programmed to turn on their receivers at a time coordinated with the emission of the timing signal 17. Thus, the wireless patient monitors 5-8 may be programmed to receive, or tune in to, the timing signal at predetermined times depending on the schedule of the timing signal emitter 3.

The wireless patient monitors 5-8 may be programmed to receive every emitted timing signal 17, or the wireless patient monitors 5-8 may only receive some of the timing signals 17. As described above, the frequency at which the wireless patient monitors 5-8 receive the timing signal may be dictated by the programming of that particular device and may depend on the accuracy of the clock in that device and/or the sample rate at which the device is currently operating. In still embodiments, one or more of the wireless patient monitors 5-8 may be constantly available to receive the timing signal 17, and thus will receive all signals emitted by the timing signal emitter 3 no matter what the period.

The timing signal emitter 3 may be any emitter capable of emitting a signal that could serve as a timing signal for the wireless patient monitors. In one embodiment, the emitter is a radio-frequency identification (RFID) emitter. Alternatively, the timing signal emitter 3 may operate in the WMTS frequency. In another embodiment, the timing signal emitter 3 is a low frequency emitter that emits signals below the wireless data transport protocol. The devices that operate in certain allocated frequency ranges, such as the WMTS, ISM, or MBANS, have the benefit of being more reliable than devices that operate on higher frequency bands, such as the unlicensed ISM frequency bands, because interference is less of an issue. For example, the timing signal emitter may operate on the MBANS (Medical Body-Area Networks Service), which occupies the 2360 MHz to 2400 MHz range, where the upper 10 MHz can be utilized outside the hospital, such as for in-home care setups. However, in other embodiments the timing signal emitter 3 may be a Wi-Fi device, or some other device operating in a higher frequency band.

The timing signal may be any signal that can indicate a precise time. In a preferred embodiment, the timing signal can indicate a very high sample frequency (or a very small period) such as 1 MHZ, or even 1 GHZ. For example, the timing signal may be a 1 MHz signal indicating the exact time that each sample should be taken for a 1 MHZ sample rate. In one embodiment, the frequency of the timing signal is equal to or greater than the fastest sample rate used by any of the wireless patient monitors associated with that timing signal emitter 3. For example, the timing signal emitter 3 may be programmed to emit a timing signal equal to the highest sample rate of any of the devices associated with it. In another embodiment, the timing signal emitter 3 simply emits a very high timing signal 17 that is guaranteed to be greater than or equal to any device that would be connected thereto. In still other embodiments, the timing signal 17 may be a lower frequency than the sample rate of the devices associated therewith. In such an embodiment, the wireless patient monitors 5-8 would compare their sample data, or the output of their sample clock, to the timing signal and insure that the sample clock acquires the requisite number of samples within the lower period of the timing signal 17. In yet another embodiment, the timing signal may be an "in-protocol" signal, such as a specialized data sequence that preempts normal data that can be used as a reference for timing.

The wireless patient monitors 5-8 may be structured to receive the timing signal 17A or 17B from the relevant timing signal emitter 3A or 3B. Thus, if the timing signal emitter 3A or 3B emits an RFID signal, the associated wireless patient monitors 5-6 or 7-8 would have an RFID receiver. The same would be the case for any other type of timing signal emitter 3, the associated wireless monitors would be equipped with the appropriate receiver. In an embodiment where the timing signal emitter 3 operates on the same frequency as the wireless network of the healthcare facility, the wireless patient monitor may have only one transceiver that communicates with both the timing signal emitter 3 and the network 10 of the healthcare facility. In such an embodiment, the wireless patient monitor may tune into the timing signal emitter 3 to receive the timing signal 17 therefrom. During that time, the wireless patient monitor may cease its wireless transmission of the patient data to the network time of the healthcare facility. In other embodiments where the timing signal emitter 3 operates on a different frequency than the wireless network of the healthcare facility, the wireless patient monitor 5-8 may have a dedicated receiver to receive the timing signal 17.

The wireless network of the healthcare facility network 10 preferably operates on the Wi-Fi band, e.g. the 2.4 GHZ band; however, the wireless network could operate on any band known in the art that can be utilized for transmitting and receiving patient physiological data, including the Wireless Medical Telemetry Service (WMTS) frequencies (608 to 614 MHZ, 1395 to 1400 MHZ, or 1429 to 1432 MHZ) or the Medical Body-Area Networks Service (MBANS) frequencies (2360 MHz to 2400 MHz). The wireless network 10 may be the wireless network of the healthcare facility, and may consist of at least one wireless access point 11, or access point, and a network server 12. The wireless access point 11 may be any receiving device capable of receiving signals from one or more of the wireless patient monitors 5-8. The wireless access point 11 is preferably a transceiver, or some other type of device having both receiving and transmitting capabilities. Or, in other embodiments the wireless access point 11 may just be a receiver.

Figure 2:
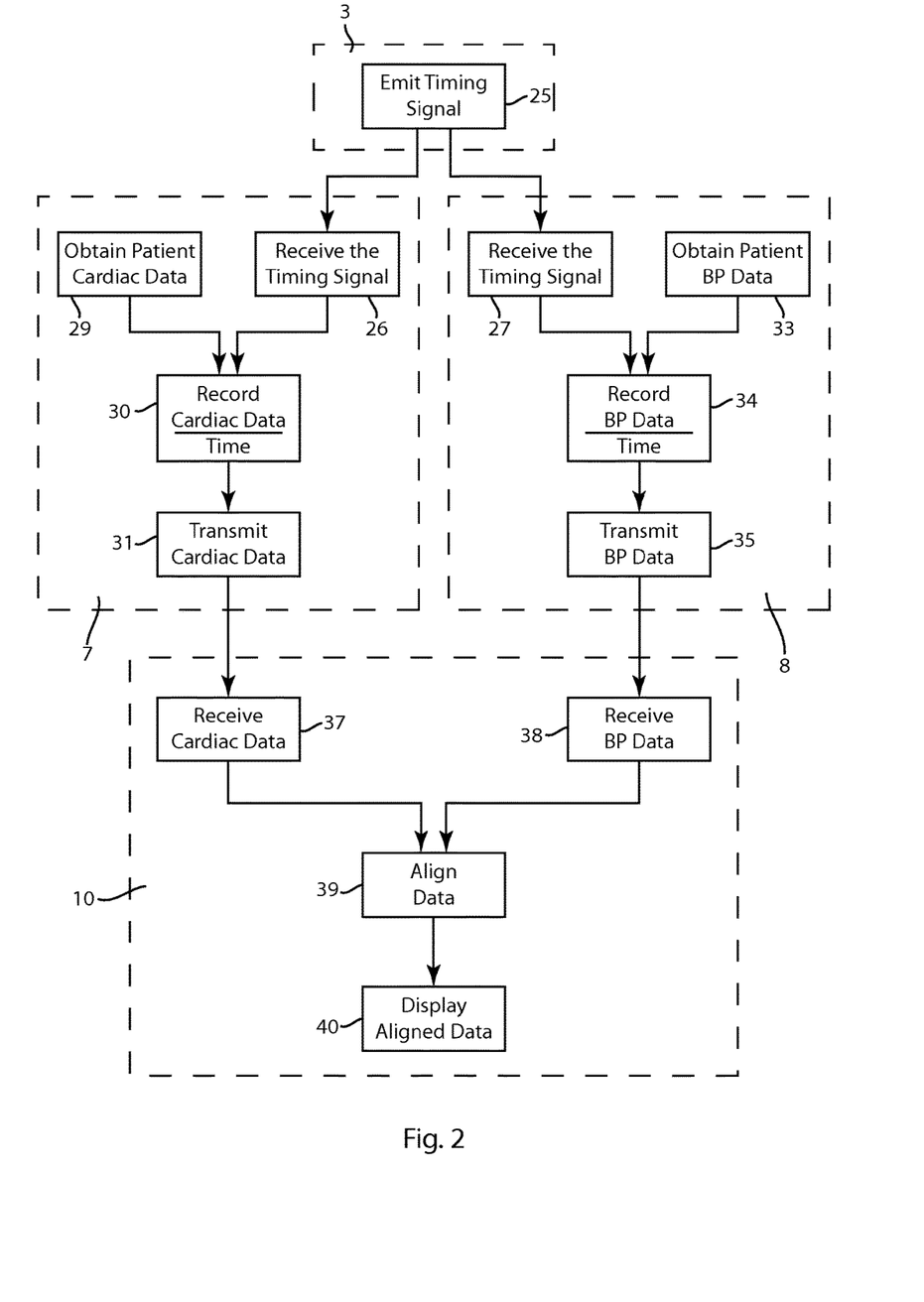
FIG. 2 depicts one embodiment of a method for wireless patient monitoring.

FIG. 2 depicts a flowchart describing one embodiment of a method executed by the wireless monitoring system 1. In that embodiment, two wireless patient monitors 7 and 8 collect data and wirelessly transmit the data to the network 10 of the healthcare facility. In the embodiment, the wireless patient monitor 7 is an ECG monitor, and the wireless patient monitor 8 is an invasive blood pressure monitor. First, a timing signal is emitted at step 25. For example, the timing signal 17 may be emitted by a timing signal emitter 3 as described above. Next, the timing signal is received at step 26 and step 27 by individual wireless patient monitors 7 and 8. In the exemplary embodiment depicted in FIG. 2, a patient cardiac signal is obtained 29, and then the cardiac data is recorded with respect to the time set by the timing signal at step 30. The recorded cardiac data is then transmitted 31 by the wireless patient monitor 7. Meanwhile, the wireless patient monitor 8 obtains a blood pressure signal 33 from the same patient, and records the blood pressure data with respect to time 34, which is defined by the timing signal received at step 27. The timing signal may provide an external clock source to the digitizers in the respective patient wireless patient monitors 7 and 8, such that the digitizers responds to the timing signal and sample the physiological signals accordingly. Alternatively, the wireless patient monitors may utilize the timing signal 17 to synchronize their internal sample clocks. The recorded blood pressure data is then wirelessly transmitted at step 35 over a wireless network.

One or more wireless receivers in the healthcare facility network 10 receives the cardiac data at step 37 and the blood pressure data at step 38. Each of the data signals received for a patient is aligned at step 39, for example when it is processed by the network server 12. The aligned data is then displayed 40, for example on a display device 14 used by a clinician 22. The aligned patient data is then provided at step 51. The aligned data may be provided to a clinician, such as on the display device. Alternatively, the aligned data could be provided to further data analysis module that process the aligned data, for example to assess the patient's condition.

Figure 3:
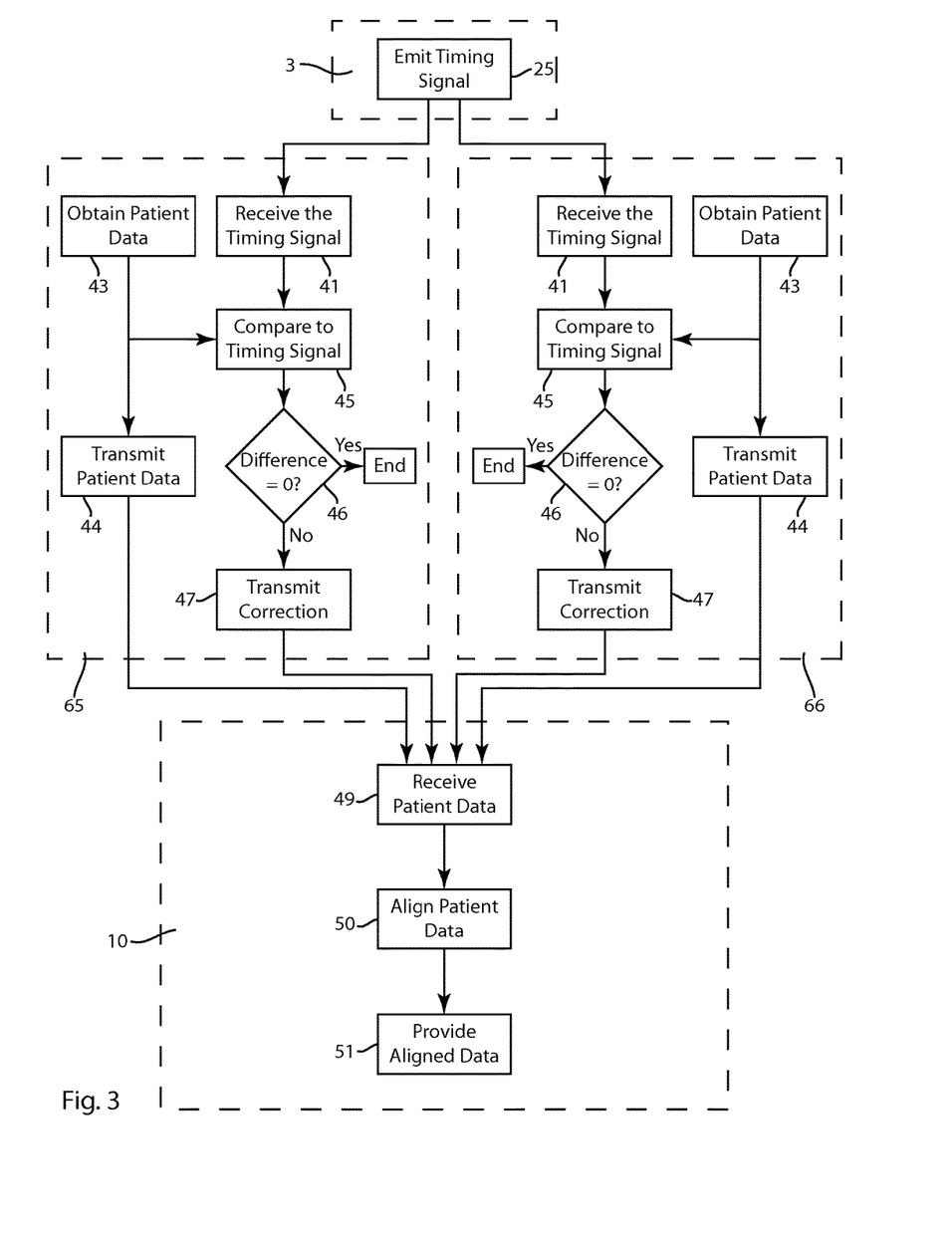
FIG. 3 depicts another embodiment of a method for wireless patient monitoring.

FIG. 3 demonstrates another embodiment of a method for wirelessly monitoring patient physiological data. A timing signal is emitted 25 and received by a first wireless patient monitor 65 and a second wireless patient monitor 66. The first and second wireless patient monitors 65 and 66 may be any type of monitors known in the art for recording and monitoring physiological data of a patient. Beginning at step 43, each wireless patient monitor 65 and 66 obtains patient data, which may be any type of physiological data recorded from the patient. The patient data is then transmitted 44 from each wireless patient monitor 65 and 66 to the healthcare facility network 10. Thus, each wireless patient monitor 65 and 66 independently gather and transmit physiological from the same patient. Each wireless patient monitor 65 and 66 also compares the timing of the gathered patient data against the timing signal to make sure that the data is synchronized. Specifically, when the timing signal is received 41, each patient monitor compares, at step 45, the timing signal to the patient data obtained at step 43. Alternatively, each patient monitor could compare the timing signal to the internal timing signal produced by the internal sample clock of each patient monitor. In still other embodiments, each patient monitor could compare the timing signal to any clock in the patient monitor that determines the sample rate or digital time stamp of the patient data obtained at step 43.

At node 46 it is determine whether there is a difference between the timing signal and the sample rate, or the sample timing, of the patient data obtained at step 43. If a difference is detected, then the patient monitor transmits a correction 47 wirelessly to the healthcare facility network 10. On the other hand, if there is no difference between the timing signal and the sampling of the patient data obtained at step 43, then the wireless patient monitor 65 or 66 will take no further action. Thus, each patient monitor checks the timing of its data collection against the timing signal 17 emitted by the timing signal emitter 3, and transmits a correction, or notification, of the discrepancy, should it exist. The step 47 of transmitting a correction may include, for example, transmitting a notification of the difference between the timing signal received at step 41 and the timing of the patient data obtained at step 43. Alternatively, the correction transmission 47 may include revised patient data, which is revised to reflect synchronization between the timing signal received at step 41 and the data obtained at step 43.

The patient data collected by each wireless patient monitor 65 and 66 is received at step 49 by the healthcare facility network 10, as is any correction transmission emitted at step 47. The network 10 then aligns the patient data 50, which includes accounting for any correction transmission emitted by any wireless patient monitor. Thus, if a wireless patient monitor emits a notification regarding a timing difference between its received timing signal and the transmitted patient data, then the processor on the network 10 will amend that transmitted data from step 44 to account for the correction transmitted at step 47. Similarly, if the correction transmitted at step 47 is adjusted patient data, and thus is different than the patient data transmitted at step 44, the processor on the healthcare network 10 will replace the patient data transmitted at step 44 with the corrected data transmitted at step 47. Additionally, the processor on the network 10 will align the patient data from each of the wireless patient monitors 65 and 66, which may include corrected patient data. The data is aligned according to time, which is dictated by the global timing signal emitted at step 25.

Figure 4:
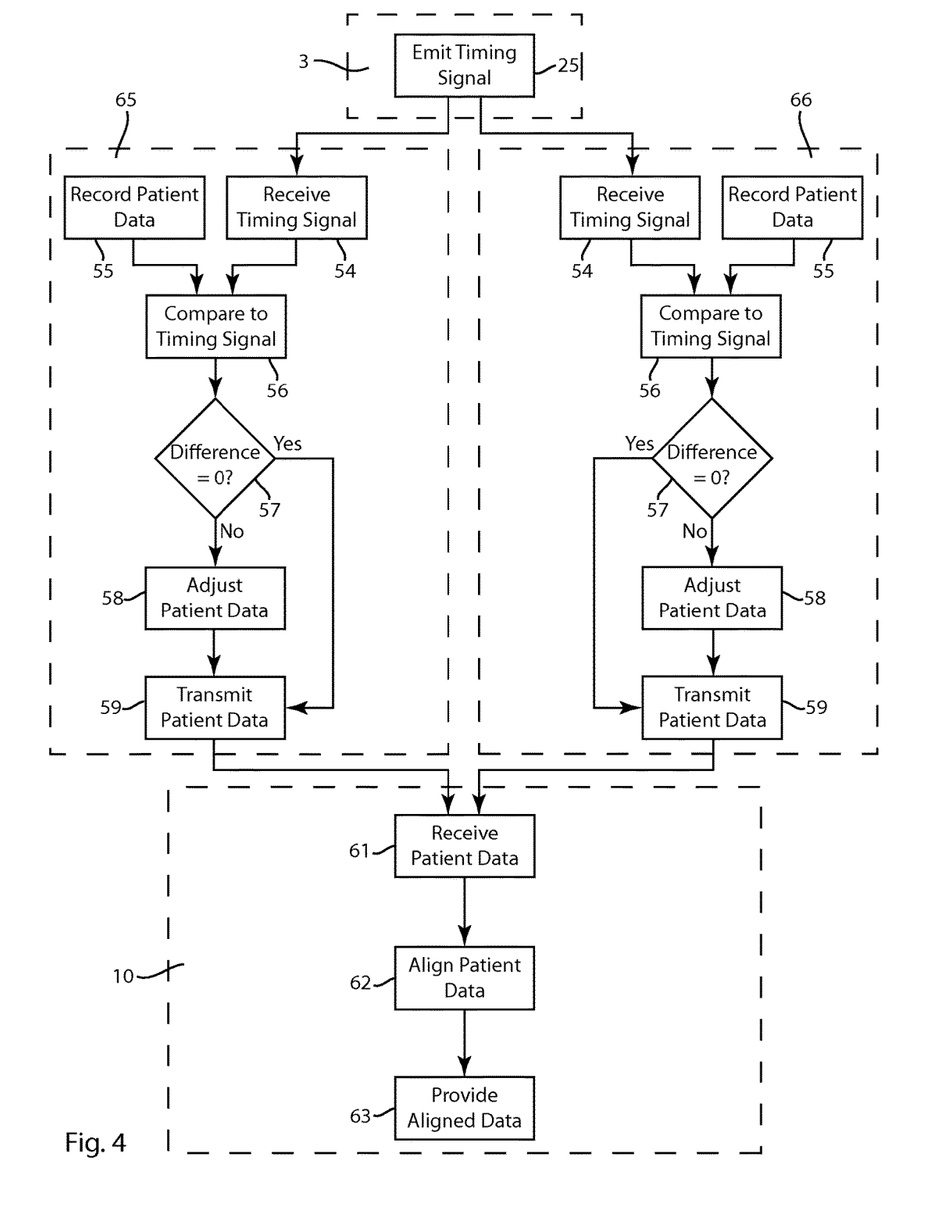
FIG. 4 depicts another embodiment of a method for wireless patient monitoring.

FIG. 4 describes another embodiment of a method of wirelessly monitoring physiological data of a patient. The timing signal is emitted at step 25 and is received at step 54 by each of the first and second patient monitors 65 and 66.

In the embodiment of FIG. 4, the patient physiological data is recorded at step 55, which is executed individually by each of the wireless patient monitors 65 and 66. Each of the wireless patient monitors then compares at step 56 the timing signal received at step 54 to the patient data recorded at step 55. Alternatively, the wireless patient monitors 65 or 66 could compare the timing signal with the step 54 to an internal clock inside the patient monitor, such as the sample clock, to see if the sampling and digital time stamping of the data recorded at step 55 coincides with the timing dictated by the timing signal. At step 57, if the difference between the timing signal and the patient data is not zero (if there is a difference between the timing communicated by the timing signal and the timing of the patient data), then the wireless patient monitor adjusts the patient data at step 58 so that the patient data is synchronized according to the timing signal. On the other hand, if the timing signal and the recorded patient data are synchronous, or aligned in time, then the wireless patient monitor does not need to adjust the patient at step 58 and will proceed directly to transmission of the patient data at step 59. Either way, the wireless patient monitor transmits the patient data, whether the adjusted patient data from step 58 or the data as recorded at step 55, over a wireless network to the healthcare facility network 10. The above described steps are executed by each of the wireless patient monitors individually, and thus the transmitted data received at the network 10 from each of the wireless patient monitors has already been synchronized by the same timing signals. Thus, the patient data received at step 61 from each of the patient monitors 65 and 66 can easily be aligned at step 62 according to the timing signal. Then, at step 63, the aligned patient data is provided as described previously.

In yet another embodiment now shown, each wireless patient monitor may record patient data and receive the timing signal from the timing signal emitter 3, and then may transmit the patient data and the received timing signal to the network 10. In such an embodiment, the network would compare the patient data to the timing signal to determine whether the data is synchronized with the timing signal. The network computer 10 may then adjust the patient data received from the wireless patient monitor to correspond with the timing signal, if necessary. Additionally, if the network 10 determines that the wireless patient monitor is not synchronized with the timing signal in its recording of patient data, the network 10 may send a correction signal to the wireless patient monitor, instructing the wireless patient monitor to adjust its clock to synchronize with the timing signal.

Figure 5:
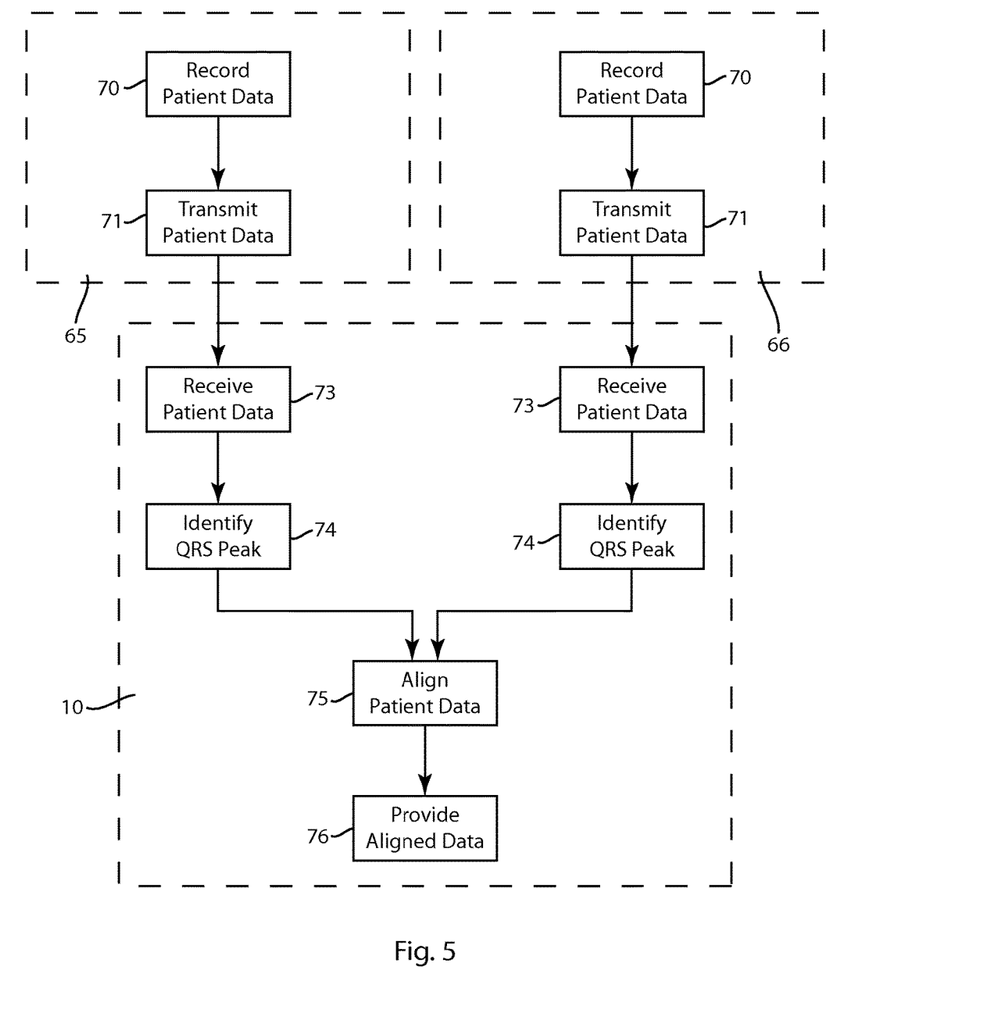
FIG. 5 depicts another embodiment of a method for wireless patient monitoring.

FIG. 5 depicts yet another embodiment of the method for wirelessly monitoring patient physiological data. Starting at step 70, physiological data is recorded from a patient by each wireless patient monitor 65 and 66. Each wireless patient monitor 65 and 66 then wirelessly transmits 71 the patient data to the network 10 of the healthcare facility. Then, the patient data is received 73 by the network 10, for example by the wireless access point 11. The received data is processed at step 74, for example by a network server 12, to identify the location in time of the QRS complexes relating to the patient's cardiac activity. The location of the QRS peaks is identified in each data set received from each of the wireless patient monitors 65 and 66, and thereby serves as a timing signal that can be used to align the patient data from each of the wireless monitors 65 and 66. For example, each of the patient data sets can be filtered to identify low frequency activity therein, for example in the range of 0 to 5 Hz, which will contain the QRS complex. Then, at step 75 each of the data sets received from the wireless patient monitor 65 and 66 can be aligned. The data sets are aligned in time by aligning the data according to the locations of the QRS peaks in each data set. The aligned data is then divided at step 76.

In another related embodiment, each wireless patient monitor 65 and 66 records the patient data at step 70 and then identifies the QRS peak(s) therein. The patient data, along with the identified QRS peaks, are then transmitted by each wireless patient monitor 65 and 66 to the network 10. In this embodiment, the network 10 could receive the patient data at step 73 and then align the patient data at step 75 according to the locations of the QRS peaks in each of the data sets identified by each of the wireless patient monitors 65 and 66.

In still other embodiments, the patient data recorded by each of the wireless patient monitors could be aligned according to a different predetermined signal element (other than QRS peak) present within the physiological data recorded at each wireless patient monitor. The timing signal could be provided by any consistent, periodic physiological signal identifiable at multiple locations across a patient's body, and specifically at the locations where patient monitors are collecting physiological data from the patient. For example, other physiological signals that may be employed as a timing signal may include other portions of the cardiac signal, including any identifiable aspect of the n-wave, the QRS complex, or the T-wave, any signal related to respiration, or any commonly detectable autonomic signal.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. A method for wirelessly monitoring physiological data of a patient, the method comprising:
   emitting a timing signal from a wireless emitter;
   receiving the timing signal at a receiver in each of at least two wireless patient monitors acquiring physiological data from the patient;
   acquiring physiological data from the patient over time at each of the wireless patient monitors, wherein the time for the physiological data is defined according to the timing signal; and
   transmitting the physiological data acquired by each of the wireless patient monitors over a wireless network of a healthcare facility.

2. The method of claim 1, further comprising the steps of:
   receiving at least two physiological data sets at a central processor from the at least two wireless patient monitors;
   aligning in time the physiological data sets from the at least two wireless patient monitors based on the time defined according to the timing signal to create an aligned physiological representation; and
   providing the aligned physiological representation to a clinician.

3. The method of claim 1, wherein the timing signal is a periodic timing signal transmitted at predefined times, and wherein the method further comprises:
comparing the periodic timing signal to a sample clock in each of the wireless patient monitors; and
if the sample clock of either of the wireless patient monitors differs from the periodic timing signal, transmitting a time correction signal over the wireless network identifying the difference between the periodic timing signal and the sample clock.

4. The method of claim 3, wherein the periodic timing signal is an RFID signal.

5. The method of claim 3, wherein the periodic timing signal is a low frequency signal not part of a standard wireless data transport protocol.

6. The method of claim 3, wherein the periodic timing signal is in the Wireless Medical Telemetry Service spectrum or the Medical Body-Area Networks Service spectrum.

7. The method of claim 1, wherein the timing signal is a periodic timing signal transmitted at predefined times, and wherein the method further comprises:
comparing the periodic timing signal to a sample clock in each of the wireless patient monitors; and
if the sample clock of either of the wireless patient monitors differs from the periodic timing signal, correcting the sample clock to correspond with the timing signal.

8. The method of claim 1, wherein the timing signal is a periodic timing signal transmitted at predetermined times, and wherein the method further comprises:
comparing the periodic timing signal to a sample clock in each of the wireless patient monitors; and
if the sample clock of either of the wireless patient monitors differs from the periodic timing signal, adjusting the physiological data acquired from the patient by that wireless patient monitor to coincide with the periodic timing signal.

9. The method of claim 8, wherein the step of transmitting the physiological data over the wireless network of the healthcare facility comprises transmitting the adjusted physiological data.

10. The method of claim 8, further including the step of transmitting the adjusted physiological data over the wireless network of the healthcare facility.

11. The method of claim 1, wherein the timing signal is a continuous signal, and wherein the sample rate of the physiological data acquired from the patient is continuously defined with respect to the timing signal.

12. The method of claim 1, wherein the step of emitting a timing signal from a wireless emitter is emitting a local timing signal for the patient that is receivable within a predefined range of a the patient.

13. A method of synchronizing physiological data acquired from a patient on two or more wireless patient monitors, the method comprising:
acquiring physiological data from the patient at each wireless patient monitor;
transmitting the physiological data from each wireless patient monitor over a wireless network of a healthcare facility;
at a central processor, identifying a timing signal within the physiological data acquired by each wireless patient monitor, wherein the timing signal is a predetermined signal element present within the physiological data acquired at each wireless patient monitor;
aligning the physiological data acquired by each wireless patient monitor according to the timing signal to create an aligned physiological representation; and
providing the aligned physiological representation to a clinician.

14. The method of claim 13, wherein the timing signal is based on a cardiac signal identifiable within the physiological data acquired at each wireless patient monitor.

15. A system for wirelessly monitoring physiological data of a patient, the system comprising:
a timing signal emitter configured to emit a timing signal that is receivable within close range of the patient;
at least one wireless patient monitor, each wireless patient monitor acquiring physiological data from the patient and having:
a sensor configured to acquire a physiological signal from the patient;
a timing signal receiver configured to receive the timing signal;
a digitizer configured to digitally sample the physiological signal acquired by the sensor to create physiological data according to the timing signal;
a wireless network transmitter configured to transmit the physiological data over a wireless network of a healthcare facility;
wherein the wireless patient monitor synchronizes the digital sampling of the physiological signal by the digitizer according to the timing signal;
a central processor configured to receive the physiological data transmitted by each of the at least one wireless patient monitor over the wireless network and align the physiological data according to the timing signal to create an aligned physiological representation; and
wherein the timing signal is continuously emitted, and wherein the timing signal defines an external sample clock that controls the digital sampling of the physiological signal by the digitizer.

16. The method of claim 15, wherein the timing signal is encoded such that it will only be utilized by wireless patient monitors configured to receive and decode the timing signal.

* * * * *